United States Patent [19]

Beattie et al.

[11] 4,150,156

[45] Apr. 17, 1979

[54] 7-(SUBSTITUTED METHYL)-3-(SUBSTITUTED THIO)-CEPHALOSPORINS, DERIVATIVES AND PHARMACEUTICAL COMPOSITIONS CONTAINING THEM

[75] Inventors: Thomas R. Beattie, North Plainfield; Lovji D. Cama, Edison; Burton G. Christensen, Scotch Plains; Frank P. Dininno, Old Bridge, all of N.J.

[73] Assignee: Merck & Co., Inc., N.J.

[21] Appl. No.: 903,455

[22] Filed: May 8, 1978

Related U.S. Application Data

[63] Continuation of Ser. No. 634,293, Nov. 21, 1975, abandoned.

[51] Int. Cl.$^2$ .................. A61K 31/545; C07D 501/00
[52] U.S. Cl. ....................................... 424/246; 544/17; 544/21; 544/22; 544/26; 544/27; 544/29; 544/90; 544/282; 424/248.53; 424/251; 424/244; 260/239 A; 260/332.2 H
[58] Field of Search ..................... 544/17, 21, 22, 26, 544/27, 29; 424/246

[56] References Cited

U.S. PATENT DOCUMENTS

| | | | |
|---|---|---|---|
| 3,714,156 | 6/1973 | Rapoport | 544/30 X |
| 3,766,177 | 10/1973 | Webber et al. | 260/243 C |
| 3,976,641 | 8/1976 | Hoover et al. | 544/26 X |
| 3,992,377 | 11/1976 | Chauvette et al. | 544/27 |
| 4,066,641 | 1/1978 | Hamashima et al. | 544/17 |

FOREIGN PATENT DOCUMENTS

| | | | |
|---|---|---|---|
| 2416492 | 10/1974 | Fed. Rep. of Germany | 544/30 |
| 2537974 | 3/1976 | Fed. Rep. of Germany | 544/29 |

Primary Examiner—Donald G. Daus
Assistant Examiner—Diana G. Rivers
Attorney, Agent, or Firm—Frank M. Mahon; Julian S. Levitt; James A. Arno

[57] ABSTRACT

Disclosed are antibiotic 3-(substituted thio)-7-(substituted methyl) cephalosporins, derivatives and analogues thereof; wherein the methyl substituent is, inter alia, hydroxyl, ketonic oxygen, imino nitrogen, amino or mercapto. Also disclosed are processes for the preparation of such compounds and their pharmaceutically acceptable salt, ester and amide derivatives; pharmaceutical compositions comprising such compounds; and methods of treatment comprising administering such compounds and compositions when an antibiotic effect is indicated.

6 Claims, No Drawings

7-(SUBSTITUTED METHYL)-3-(SUBSTITUTED THIO)-CEPHALOSPORINS, DERIVATIVES AND PHARMACEUTICAL COMPOSITIONS CONTAINING THEM

This is a Continuation of U.S. patent application Ser. No. 634,293, filed Nov. 21, 1975, now abandoned.

BACKGROUND OF THE INVENTION

This invention relates to a new class of antibiotics which may be generically represented by the following structural formula (I):

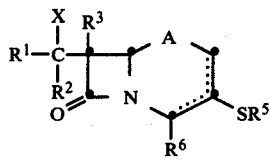

wherein the dotted line indicates provision for both $\Delta^2$ and $\Delta^3$ embodiments; A is S, O, CH$_2$, SO, or NR$^7$ (R$^7$ is selected from the group consisting of hydrogen, alkyl, formyl, acyl, thioacyl, alkylsulfonyl and arylsulfonyl); X is OH, =O, SH, =NH, NH$_2$, or NHR$^7$; R$^1$ and R$^2$ are independently selected from the group consisting of hydrogen; substituted and unsubstituted: alkyl; aryl; aralkyl; heteroaryl and heteroaralkyl (mono- and bicyclic) wherein the heterocyclic moiety comprises 4–10 ring atoms and the hetero atom (or atoms) is O, N or S; and wherein the ring or chain substituent is selected from: amino, carboxy, hydroxy, alkoxy, carbalkoxy, lower alkyl, heteroaryl, and substituted amino such as mono- and di-alkylamino, and acylamino; and per-haloalkyl; examples of such substituents, R$^1$ and R$^2$, are: methyl, tri-fluoromethyl, phenyl, substituted phenyl, benzyl and the like; R$^3$ is selected from the group consisting of hydrogen, alkoxy, alkylthio and halogen such as fluoro and bromo; R$^5$ is selected from the group consisting of hydrogen; substituted and unsubstituted: alkyl; aryl; aralkyl, heteroaryl and heteroaralkyl wherein the heterocyclic moiety comprises 4–6 ring atoms and the hetero atom (or atoms) is O, N or S; wherein the ring on chain substituent is selected from: amino, carboxy, hydroxy, alkoxy, carbalkoxy, lower alkyl, heteroaryl, and substituted amino such as mono- and di-alkylamino, and acylamino; examples of such substituents, R$^5$ are: β-aminoethyl, β-hydroxyethyl, phenyl, substituted phenyl, benzyl, phenethyl and the like; and R$^6$ is selected from the group consisting of PO(OH)$_2$, SO$_2$(OH), SO$_2$NH$_2$ and derivatives thereof, [see copending, commonly assigned U.S. patent application, Ser. No. 410,831 filed Nov. 8, 1973, incorporated herein by reference for definition of R$^6$], and COXR$^8$ wherein X is oxygen or sulphur and R$^8$ is, inter alia, representatively selected from the group consisting of hydrogen, trialkylsilyl, and the pharmaceutically acceptable salt, ester and amide moieties known in the antibiotic bicyclic β-lactam art such as sodium, potassium, pivaloyloxymethyl, and the like.

There is a continuing need for new antibiotics. For, unfortunately, there is no static effectiveness of a given antibiotic because continued wide scale usage of any such antibiotic selectively gives rise to strains of pathogens which are resistant to the exploited antibiotic. In addition, the known antibiotics suffer from the disadvantage that they are only effective against certain types of microorganisms. Accordingly, the search for new antibiotics has continued.

unexpectedly, it has been discovered that the compounds of the present invention are broad spectrum antibiotics, which are useful in animal and human therapy and in inanimate systems. It will be recognized from the above generic representation (I) that the principal novel features of the compounds of the present invention are the substituents at the 7- and 3-positions. It will also be noted, except where expressly stated, that the balance of the cephalosporin or cephalosporin-like structure (I) is well-known in the relevant art; likewise the substituents R$^3$ and R$^6$ are well-known as exemplified by the following U.S. Patents and co-pending, commonly assigned U.S. patent applications which are incorporated herein by reference [U.S. patent application, Ser. No. 410,831 filed Nov. 8, 1973].

Thus it is an object of the present invention to provide a novel class of antibiotics which includes, inter alia, species having the basic nuclear structure of the cephalosporins but which are characterized by having a substituted thio radical at the 3-position of the six-membered ring and a substituted methyl radical at the 7-position of the β-lactam ring. These antibiotics are active against a broad range of pathogens, which representatively include gram positive bacteria such as *Staphylococcus aureus, Streptococcus pyogenes,* and gram negative bacteria such as E. coli and Salmonella and *Proteus mirabilis* and *Proteus morganii.* Further objects of this invention are to provide chemical processes for the preparation of such compounds; intermediates useful in preparing such compounds; pharmaceutical compositions comprising such compounds; and to provide methods of treatment comprising administering such compounds and compositions when an antibiotic effect is indicated.

DETAILED DESCRIPTION OF THE INVENTION

The following U.S. Patents and co-pending, commonly assigned U.S. Patent Applications are incorporated herein by reference for the subject matter which they disclose as it relates to the preparation of necessary starting materials needed for a description of the present invention. It will be noted that these patents and applications disclose the basic nucleii (IIa, IIb, IIc) (and derivatives thereof) upon which the present invention relies:

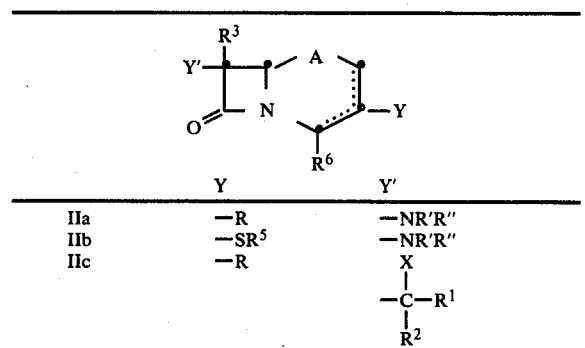

wherein all substituents, except R, R' and R" are as previously defined; and R is selected from the group consisting of hydrogen, acyloxymethyl such as acetoxymethyl and carbamoyloxymethyl, and halomethyl for example; and R' and R" are independently selected from the group consisting hydrogen and the acyl radicals known in the bicyclic β-lactam antibiotic art. The incorporated-by-reference materials are: co-pending, commonly assigned, concurrently filed U.S. patent applications Ser. Nos. 634,082 (Beattie, et al.) and 634,081 (Cama, et al.) which relate, respectively, to 7-(substituted methyl)cephalosporins and 3-(substituted thio)-cephalosporins, and both now abandoned.

With reference to structure I, above-given, the preferred embodiments of the present invention are those wherein:

A is selected from S, $CH_2$, O;

$R^1$ and $R^2$ are independently selected from hydrogen, alkyl, aryl, such as phenyl, substituted phenyl, and aralkyl such as benzyl, β-phenethyl and heteroaralkyl such as 2-thienylmethyl;

X is selected from the group consisting of OH, =O, =NH, $NH_2$, SH and $NHR^7$;

$R^3$ is selected from hydrogen, alkoxy such as methoxy, and lower alkylthio such as methylthio, and halogen such as fluoro and bromo;

$R^5$ is hydrogen, formyl or $(CH_2)_nY$ wherein Y is hydrogen, hydroxyl, halo, mercapto, acyloxy, acylthio, substituted hydroxy, carboxy, carbalkoxy, substituted mercapto, a quaternary ammonium group, azido, amino or an N- substituted amino group; and n is an integer from 1 to 6 and preferably 1 to 3. Thus, $(CH_2)_nY$ can be haloethyl such as chloroethyl, bromomethyl or fluoroethyl.

When Y is a substituted hydroxy or substituted mercapto group, $R^5$ can be shown by the formula $$-(CH_2)_nZR'$$

where Z is oxygen of sulfur, and R' is an acyl group; a straight chain or branched chain loweralkyl, alkenyl or alkynyl group; an aryl group; an aralkyl group; or a heterocyclic group such as heteroaryl or heteroalkyl. These groups can be unsubstituted or can be substituted by radicals such as alkyl, alkoxy, halo, cyano, carboxy, carbamoyl, azido, sulfo, amino, substituted amino, haloalkyl, carboxyalkyl, carbamoylalkyl, N-substituted carbamoylalkyl, guanidino, N-substituted guanidino, guanidoalkyl, sulfamyl, substituted sulfamyl, and the like. Representative of the groups thus represented that might be mentioned are methoxymethyl, n-propoxymethyl, methylthiomethyl, acetoxymethyl, propionyloxymethyl, benzoyloxymethyl, (p-chlorobenzoyl)oxymethyl, (p-methylbenzoyl)oxymethyl, pivaloyloxymethyl, (1-adamantyl)carboxymethyl, butanoyloxymethyl, carbamoyloxymethyl, (N-methylcarbamoyl)oxymethyl, (N-ethylcarbamoyl)oxymethyl, [N-(2-chloroethyl)carbamoyl]oxymethyl, (N-phenylcarbamoyl)oxymethyl, (N-p-sulfophenylcarbamoyl)oxymethyl, p-carboxy methylphenylcarbamoyloxymethyl, methoxycarbonyloxymethyl, isobutanoyloxymethyl, cyclobutylcarbonyloxymethyl, carbamoylthiomethyl, (ethoxythiocarbonyl)thiomethyl, (n-propoxythiocarbonyl)thiomethyl, (cyclopentanoxythiocarbonyl)thiomethyl methylthiomethyl, N,N-diethylthiocarbamoylthiomethyl, N-methylpiperazinium-1-thiocarbonylthiomethyl, N,N-dimethylpiperazinium-1-thiocarbonylthiomethyl, 2-furoylthiomethyl, Isothiouronimmethyl, (5-methyl-1,3,4-thiadiazol-2-yl)thiomethyl, p-tolylsulfonylthiomethyl, mesyloxymethyl, 1-methyl-1,2,3,4-tetrazolyl-5-thiomethyl, tosyloxymethyl, sulfamoyloxymethyl, 1-naphthoyloxymethyl, 2-furylacetoxymethyl, cinnamoyloxymethyl, p-hydroxycinnamoyloxymethyl, p-sulfocinnamoyloxymethyl and 1R:2S-epoxypropylphosphonyloxymethyl.

The substituent $(CH_2)_nY$ can also be a group of the general formula:

$$-(CH_2)_nY_1$$

wherein $Y_1$ represents amino or substituted amino including nitrogen heterocycles and substituted heterocyclic groups. Examples of such groups that might be mentioned are aminomethyl, acetamidomethyl, carbamoylaminomethyl, N,N-dimethylaminomethyl, N-(2-chloroethyl)aminomethyl, 5-cyanotriazol-1-ylmethyl, 4-methoxycarbonyltriazol-1-ylmethyl.

Representative of the quaternary ammonium groups representing Y that might be mentioned are pyridinium, 3-methylpyridinium, 4-methylpyridinium, 3-chloropyridinium, 3-bromopyridinium, 3-iodopyridinium, 4-carbamoylpyridinium, 4-(N-hydroxymethylcarbamoyl)pyridinium, 4-(N-carbomethoxycarbamoyl)pyridinium, 4-(N-cyanocarbamoyl)pyridinium, 4-(carboxymethyl)pyridinium, 4-(hydroxymethyl)pyridinium, 4-(trifluoromethyl)pyridinium, quinolinium, picolinium and lutidinium.

The preferred groups representing Y are hydrogen, halo, azido, cyano, hydroxy, alkoxy, aryloxy, aralkyloxy, heterocycloxy, mercapto, alkylthio, arylthio, aralkylthio, heterocyclythio, amino, alkylamino, alkanoylamino, hydroxyphenyl, acylthio, acyloxy, isothiouronium, sulfamoyloxy, quaternary ammonium, a heterocyclic tertiary amine, alkylsulfonyloxy and (cis-1,2-epoxypropyl)phosphonyloxy. The heterocycles can be a 5 or 6 membered hetero ring containing one or more nitrogen, oxygen or sulfur atoms. The acyl group can be a loweralkanoyl group of 2-6 carbon atoms, carbamoyl, or thiocarbamoyl and N-alkyl or N,N-dialkyl derivatives thereof. The alkyl group of the foregoing substituents contains 1-6 carbon atoms and may be further substituted radicals such as alkoxy, halo, amino, cyano, carboxy, sulfo, and the like.

$R^6$ is $COXR^8$ wherein X is oxygen or sulfur, and $R^8$ can be alkyl having 1-10 carbon atoms, straight or branched, such as methyl, ethyl, t-butyl, pentyl, decyl, etc.; substituted alkyl, wherein the alkyl portion has 1-10 carbon atoms but is preferably methyl or ethyl; and the substituent can be a heterocyclic structure having 1-3 hetero atoms of either O, N, or S; such as phthalimidomethyl, succinimidomethyl, phenacyl, p-bromophenacyl, (2-thienyl)methyl, (6-indenyl)methyl, acetoxyacetylmethyl, carboxymethyl, ethoxyethoxyethyl, (2-methylamino)ethyl, (2-diethylamino)ethyl, 2-(p-methylphenyl)sulfonylethyl, 2-(p-methylphenyl)ethyl, (2-acetamido)ethyl, etc. The substituent on the alkyl group can also be carboxyl, e.g., $R^8$ is α-carboxy-β,β-dimethylpropyl; alkoxyalkyl wherein the alkoxy portion has 1-10 and preferably 1-6 carbon atoms, but can be branched. Straight, or cyclic, and the alkyl portion has 1-6 carbon atoms, such as methoxymethyl, ethoxymethyl, isopropoxmethyl, decyloxymethyl, ethoxypropyl, decyloxypentyl, cyclohexyloxymethyl, etc.; alkanoyloxyalkyl wherein the alkanoyloxy portion is straight or branched and has 1-6 carbon atoms and the alkyl portion has 1-6 carbon atoms, such as acetoxymethyl, pivaloyloxymethyl, acetoxyethyl, propionyloxyethyl, acetoxypropyl, etc.; haloalkyl wherein halo is chloro, bromo, fluoro, or iodo, and the alkyl portion is straight or branched having 1-6 carbon atoms, e.g., 2,2,2-trichloroethyl, trifluoroethyl, 2- bromopropyl, diiodomethyl, 2-chloroethyl, 2-bromoethyl, etc.; alkenyl having 1-10 carbon atoms, either straight or branched, e.g. allyl, 2-propenyl, 3-butenyl, 4-pentenyl, 2-butenyl, 3-pentenyl, 3-methyl-2-butenyl, methallyl, etc.; alkynyl having 1-10 carbon atoms, either straight or branched, e.g. 3-pentynyl, propargyl, ethynyl, etc.; alkanoyl, either straight or branched, having 1-10 carbon atoms, such as pivaloyl, acetyl, propionyl, etc; aralkyl wherein alkyl has 1-3 carbon atoms, such as benzyl, benzhydryl, and substituted benzyl or benzhydryl, e.g., o-nitrobenzyl, 3,4-dinitrobenzyl, p-methoxybenzyl, p-nitrobenzyl, 3,5-dichloro-4-hydroxybenzyl, p-methoxybenzhydryl, p-carboxybenzyl, the latter being either the free acid or the sodium salt, 2,4,6-trimethylbenzyl, p-(sodiumcarboxylate)benzyl, p-methylbenzyl, or phenylethyl, 2-(p-methylphenyl)ethyl, p-t-butylbenzyl, m-phenoxybenzyl, p-pivaloyloxybenzyl, and the arylthioalkyl analogues; aryloxyalkyl wherein aryl is preferably a phenyl ring having 0-3 substituents, preferably 0 or 1 substituents in the ortho or para positions and alkyl is 1-6 carbon atoms, e.g., (4-methoxy)phenoxymethyl, phenoxymethyl, (4-chloro)phenoxymethyl, (4-nitro)phenoxymethyl, (4-benzyloxy)phenoxymethyl, (4-methyl)-phenoxymethyl, (4-benzyloxy)phenoxymethyl, (4-methyl)phenoxymethyl, (2-methoxy)phenoxymethyl, (1-phenoxy)ethyl, (4-amino)phenoxymethyl, (4-methoxy)phenylthiomethyl, (4-chloro)phenylthiomethyl, phenylthioethyl; aryl wherein aryl is phenyl or substituted phenyl having 0-3 substituents, preferably 0 or 1 substituent in the ortho or para position, e.g., (4-methyl)phenyl, (4-hydroxy)phenyl; aralkenyl wherein aryl is phenyl and alkenyl has 1-6 carbon atoms, such as 3-phenyl-2-propenyl aralkoxyalkyl wherein aralkoxy is benzyloxy, and alkyl has 1-3 carbon atoms, such as benzyloxymethyl, (4-nitro)benzyloxymethyl, (4-chloro)-bezyloxymethyl; alkylthioalkyl wherein the alkylthio portion has 1-10 and preferably 1-6 carbon atoms, but can be branched, straight, or cyclic, and the alkyl portion has $1\alpha 6$ carbon atoms, such as methylthioethyl, ethylthioethyl, cyclohexylthiomethyl, decylthiobutyl, methylthiopropyl, isopropylthioethyl, methylthiobutyl, etc.; or monocyclic aryl wherein aryl is phenyl, or substituted phenyl such as p-nitrophenyl, 3,5-dinitrophenyl, or p-carboxyphenyl, the latter having either the free acid or the sodium salt form.

In addition to the esters listed above, amides can also be employed, i.e., wherein X is the

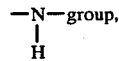

and $R^8$ is as defined.

Particularly preferred esters are those in formula I wherein X is oxygen and $R_8$ is aralkyl, aryloxyalkyl, aralkoxyalkyl, alkythioalkyl, haloalkyl, or alkenyl.

It will be apparent from a further reading of this application that in many of the chemical reactions described, the cephalosporin is blocked at position 4 by a so-called "easily removable blocking group". Many of these groups are contained within the above definition of the chain $-COXR^8$. However, it has been found more convenient to use only relatively a few of these groups during such chemical reaction, then to move the group to the free acid, and subsequently to react the latter with the desired alcohol to yield the suitable ester.

In this connection, it is noted that preferred "blocking groups" include the sub-generic groups defined above as aralkyl, haloalkyl, alkanoyloxyalkyl, alkoxyalkyl, alkenyl, substituted alkyl, or aralkoxyalkyl, and also including mono-, di-, and trialkyl-silyl wherein alkyl has 1-10 carbon atoms.

More specifically, preferred "blocking groups" include benzyl, phenacyl, methoxymethyl, trichloroethyl, trimethylsilyl, p-bromophenacyl, p-bromophenyl, benzoylmethyl, p-nitrobenzyl, pmethoxybenzyl, benzhydryl. These blocking groups are preferred since they are generally recognized easily removable blocking groups in cephalosporin and pencillin art. Although we describe procedures for the removal of these blocking groups, such processes are considered within the skill of those in the art.

On the other hand, the novel cephalosporins of this invention are best utilized pharmacologically as either the free acid in the form of commoly used, non-toxic pharmaceutically acceptable salts, or certain of the above listed esters. For instance, esters belonging to the groups defined as aralkyl, alkylthioalkyl, or alkenyl yield final products having outstanding oral activity. More specifically, high oral activity of the novel cephalosporins is obtained when $R^8$ is (2-methylthio)ethyl, pivaloyloxymethyl, 3-buten-1-yl, p-pivaloyloxybenzyl p-butylbenzyl or benzyl.

By the term "non-toxic pharmaceutically acceptable salts" is meant salts that are suitable for isolating, purifying and/or marking purposes, for example salts with bases or with acids, as well as inner salts. Salts with bases are in the first place metal salts, especially alkali metal salts, for example sodium or potassium salts, or alkaline earth metal salts, for example magnesium or calcium salts, or ammonium salts, including ammonium salts with organic bases such as tri-lower alkyl-amine, for example trimethylamine or triethylamine, or N-lower alkylazacycloalkanes, for example 1-methyl-pyrrolidine or 1-ethyl-piperidine, also dibenzylethylenediamine or procaine. They are obtained, for example, by treating the free compounds or inner salts with the basic compounds, as desired with the aid of an ion exchange resin.

Acid addition salts are in the first place those with strong inorganic acids, such as hydrochloric, hydrobromic or sulphuric acid, or with strong organic acids such as strong organic sulphonic acids, for example methanesulphonic, 2-hydroxyethanesulphonic or p-toluenesulphonic acid, or with a strong organic carboxylic acid, for example trifluoroacetic acid. They can be obtained, for example, by treating the free compounds with the appropriate strong acids if desired with the aid of an ion exchange resin.

Inner salts, which appear as hybrid ions, are obtained by treating an acid addition salt with an appropriate, weakly basic ion exchange resin, or by titrating with a base up to the isoelectric point, or from a salt with a base by treatment with acid.

The most preferred embodiments of the present invention are those having the following structure:

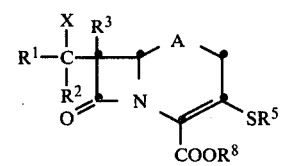

wherein A is S, O or Ch₂;

$R^1$ and $R^2$ are independently selected from the group consisting of hydrogen, substituted and unsubstituted lower alkyl having from 1-6 carbon atoms; ring and chain substituted aryl, aralkyl and heteroaralkyl such as phenyl, benzyl, phenethyl, 1-hydroxy-, 1-amino-, 1-carboxy-ethylbenzene, thienylmethyl and the like; wherein the ring and chain substituents are selected from the group consisting of COOH, $NH_2$, OH and the like;

X is OH, $-NH_2$ and $-SH$;

$R^3$ is selected from the group consisting of H, or methoxyl; and $R^5$ and $R^8$ are as previously defined.

In general the novel antibiotics of the present invention are prepared by a synthesis scheme involving two basic steps: (1.) derivatization at the 7-position; and (2.) derivatization at the 3-position. Both steps are highly regio-specific and it is not critical as to which is performed first. However, it is preferred that the derivatization at the 7-position of the β-lactam ring be performed first. These steps, as they define the total reaction scheme, are illustrated below in the preferred sequence.

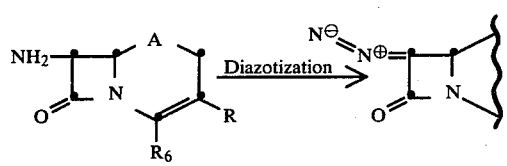

R = R or $SR^5$

Halogenation

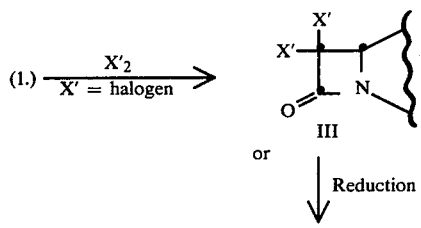

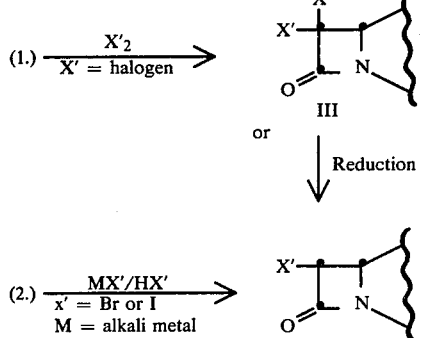

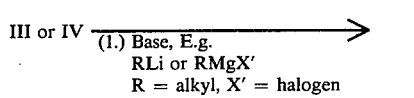

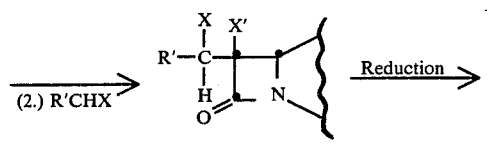

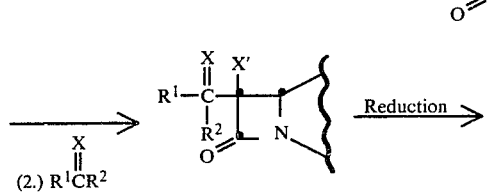

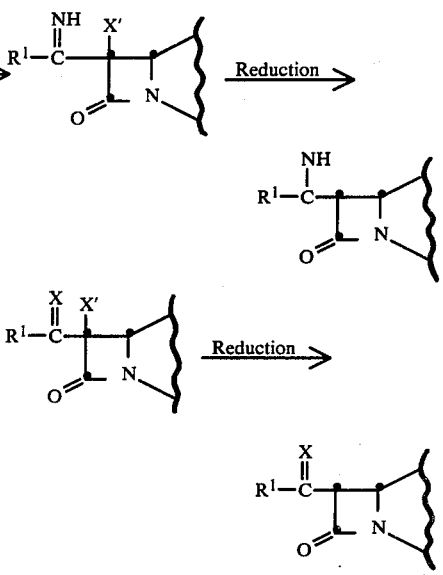

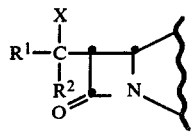

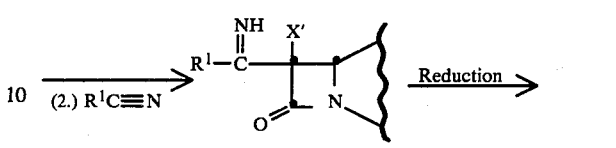

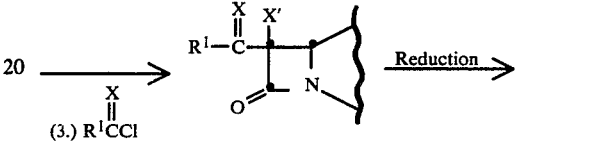

In words relative to the above reaction diagram, the free 7-amino species, Ia, is diazotized by conventional procedures such as by reaction with $NaNO_2$ in the presence of acid such as 2-N-sulfuric acid in a solvent such as methylene chloride or the like at a temperature of from 0° C. to about 25° C. for from a few minutes to four hours. The resulting diazo derivative, Ib, isolated by conventional procedures such as extraction followed by organic solvent removal, is then halogenated by either of two procedures. Both are well-known. The first procedure provides the 7,7,-dihalo species, III, and involves direct halogenation, such as bromination, in a solvent such as methylene chloride or the like at a temperature of from −78° C. to about 0° C. for from a few minutes to about 4 hours. The second procedure provides the mono halo species, IV, preferably the 7-iodo or 7-bromo species and is conducted in a polar solvent such as water, acetone, alcohol or aqueous mixtures thereof in the presence of the halide salt and its corresponding acid. The reaction is conducted at from 0° C. to about 25° C. for from a few minutes to 4 hours. Products, III and IV, if desired are separated by conventional procedures involving solvent extraction, concentration, and chromatography. It should be noted that III is convertible to IV by reduction. A particularly suitable reduction is effected by a Zn and Ag couple in methanol according to reported procedures, such as Clark, et al., J. Org. Chem., 38, 3658 (1973); alternatively catalytic hydrogenation employing Pd/C, $Pd/CaCO_3$ or $PtO_2$ in solvents such as alcohol, ethyl acetate, or dioxane at about 0° C. to 25° C. under 1 to 50 atmospheres of hydrogen.

Intermediate products, III and IV, are converted to the final products of the present invention by contacting either with a base such as an organo metallic base such as a lithium alkyl or a Grignard reagent $RMgX'$ wherein R is alkyl, aryl or the like and $X'$ is halogen such as bromo and thereafter adding to the reaction mixture the reagent of choice to give the desired final product. The reagents, as shown in the diagram are: H₂CO, R¹CHX,

and R¹C≡N; wherein R¹ and R² are as defined above, and X is oxygen or sulphur. Typically the reaction is conducted in a solvent such as tetrahydrofuran, ether, dimethoxyethane, or mixtures thereof or the like at a temperature of from −100° C. to about 0° C. for from a few minutes to about 4 hours. Typically, the organo metallic base is added first. Products derived from the 7,7-dihalo species, III, yield the illustrated halo hydrins which are reduced to the final products, I, by convention techniques such as catalytic reduction or zinc-silver couple in methanol.

It is to be noted that the above reaction scheme is regio-specific for the 7-position and that there are no criticalities of reaction parameters other than those set forth above and elaborated upon in the following specific examples. It should be further noted that the above-described procedure provides all embodiments of the present invention except those wherein R³ is other than hydrogen. When R³ is alkoxyl or alkylthio such as methoxyl of methylthio, the above procedure is modified by a subsequent procedure which involves derivatization of the 7-substituted methyl species (R=H) to form those species of the present invention wherein R³ is, for example, methoxyl.

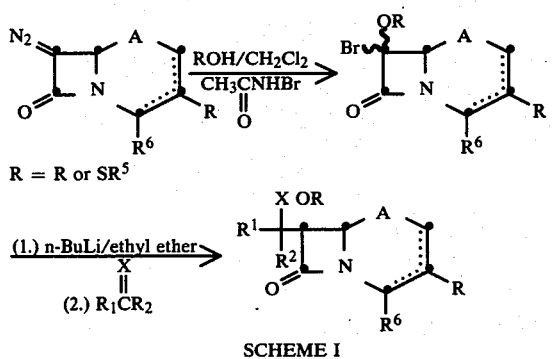

SCHEME I

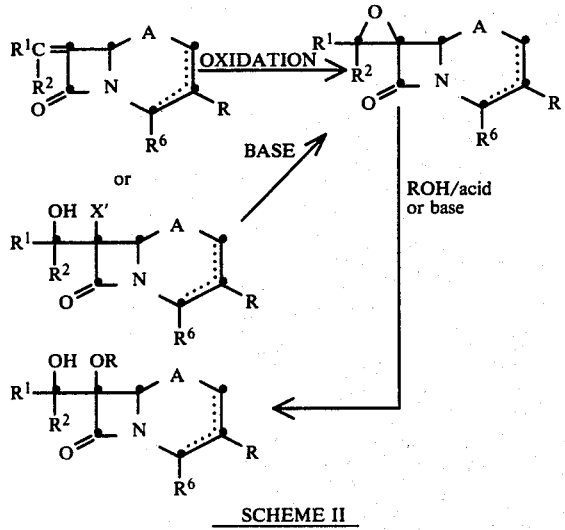

SCHEME II

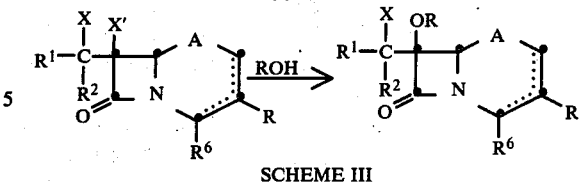

SCHEME III

With respect to the above Schemes I–III, all symbolism is as previously defined and ROH (which may also be RSH) designates a lower alkanol (or loweralkyl thiol); thus in the final products —OR designates the substituent R³.

In Scheme I, the diazo starting material is available to the art. Typically, the first step of the reaction is conducted in a solvent medium such as ROH or a mixture (ROH/CH₂Cl₂:1-1) of ROH and a solvent such as CH₂Cl₂, acetonitrile, benzene, or the like containing 1 to about 3 equivalents of a brominating agent such as N-bromoacetamide, N-bromosuccinimide, or the like; typically the reaction is conducted at from about 0° to about 50° C. for from a few minutes to several hours. The resulting 7-bromo-7-R³ species are known as in the above described process. The 7-bromo-7-R³ species is then treated with a base (1.0 to 1.5 equivalents) such as organo-metallic base, for example, n-butyl lithium, methylmagnesium bromide or the like in a solvent such as diethyl ether, tetrahydrofuran, dimethoxyethane or the like at a temperature of from −80° C. to about 0° C.; and thereafter adding, as above-described, the reagent of choice (R'CHX, $$\overset{X}{\underset{R'CR^2,}{\|}} \quad \overset{X}{\underset{R'CCl,}{\|}} \quad \overset{X}{\underset{HCH}{\|}}$$

or R'C≡N) to give the desired final product.

The epoxide of Scheme III may be prepared by treatment of the olefin with an oxidizing agent such as a peracid or peroxide or directly from the 6-halo species by treatment with base. The resulting epoxide is then converted to the desired product by treatment with ROH in the presence of acid or base. Suitable oxidizing agents are alkaline hydrogen peroxide or m-chloroperbenzoic acid. Typically the oxidation is conducted with m-chloroperbenzoic acid in a solvent such as methylene chloride, benzene, dioxane, or tetrahydrofuran at a temperature of from −20° C. to about 50° C. for from a few minutes to six hours. Direct conversion of the 7-halo species to the oxide is effected in solvents such as methanol, methylene chloride, acetonitrile and tetrahydrofuran in the presence of 1.0 to 2.0 equivalents of a base such as sodium methoxide, triethylamine, lithium diisopropylamide and sodium hydride at −20° C. to 50° C. for from a few minutes to six hours. Conversion of the oxide to the desired product is typically conducted in the alcohol of choice or in a mixture of the alcohol with a solvent such as methylene chloride, acetonitrile, benzene or tetrahydrofuran in the presence of a base (1 to 2 equivalents) such as sodium methoxide or triethylamine at −78° to 22° C. for from a few minutes to six hours. The oxide may be converted to the desired product by treatment in acidic solution. It is to be noted that the olefin starting material is known.

Scheme III is conducted by treating the 6-halo species in the alcohol of choice, for example methanol, ethanol, or a mixture of alcohol with some other solvent, as described above, with a reagent such as silver tetrafluoroborate at a temperature of from 0 to 50° C. for a few minutes to overnight.

The second major step in the total scheme may be represented by the following reaction wherein R' is $R^1R^2C(X)$— (or is $NH_2$) or conventional acyl amino, when this second step is applied in reverse order with the above-illustrated first step:

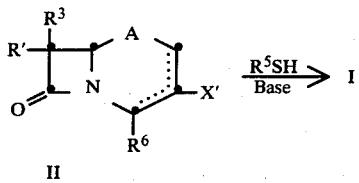

wherein X' is a leaving group selected from the group consisting of halogen, such as chloro, bromo or iodo, or $OSO_2R$ wherein R is alkyl or aralkyl such as, p-toluenesulfonic acid, trifluoromethylsulfonic acid, and methanesulfonic acid.

In words relative to the above reaction, the 3-substituted cephalosporin reactant (II) is treated with the thiol of choice, $R^5SH$, in the presence of base. Suitable bases may be selected from tertiary amines and inorganic bases such as triethylamine, pyridine, diisopropylethylamine, sodium hydride and the like. Suitable solvents for the reaction include, representatively, $CH_2Cl_2$, $CHCl_3$, tetrahydrofuran (THF), $CH_3CN$, dimethylformamide (DMF) benzene, acetonitrile, acetone and the like. Typically the reaction is conducted at a temperature of from about 0° C. to reflux for from about a few minutes to 18 hours.

It is to be noted that the above reaction scheme is regio-specific for the 3-position and that there are no criticalities of reaction parameters other than those set forth above and elaborated upon in the following examples.

Suitable starting materials (II) are known in the art. See for example *J. Chem. Soc. Chem. Comm.*, 1972, 800 and above-cited U.S. Patent application Ser. No. 410,831 (Nov. 8, 1973); Tetrahedron Letters 1972, 2341 and 3241 (Ochiai, et al.; *J.A.C.S.* 96 4986 (1974) Chauvette et al.); and Helv. 57 (1919 (1974) (Scartazzini), which references are incorporated herein by reference. Alternatively, the starting materials are conveniently prepared according to the following reaction scheme:

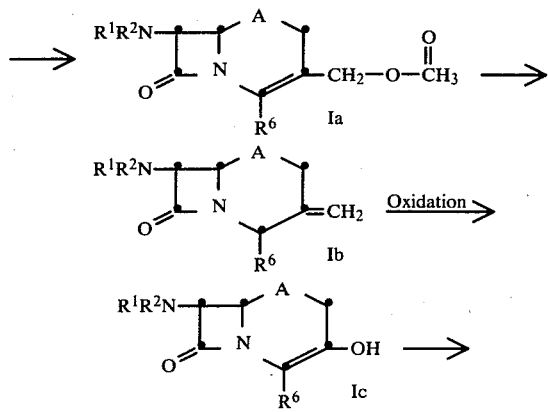

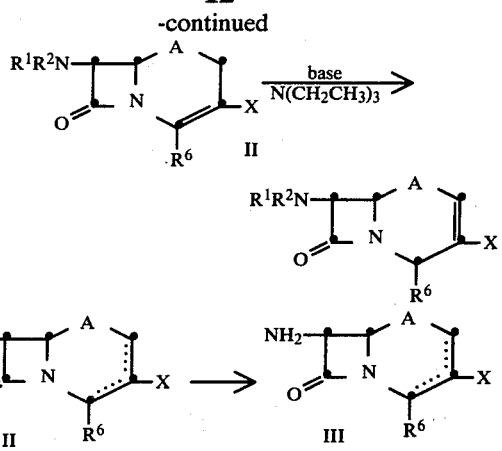

In words relative to the above diagram, the 3-methylidene species is obtained from the 3-acetoxymethyl species by reduction with CrOAc, electrolytic reduction, or displacement of OH by

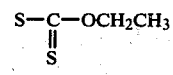

and Raney Nickel desulfurization of the product, such procedures are known in the art. Oxidation of the 3-methylidene species with, for example ozone, provides the 3-hydroxyl species. Typically the oxidation is conducted in solvents such as $CH_2Cl_2$, $CHCl_3$, ethyl acetate and the like at a temperature of from $-78°$ C. to $25°$ C. for from a few minutes to 2 hours. The resulting 3-hydroxy species is converted to the desired 3-X species (II) by, depending upon the identity of X desired, reacting it with the appropriate reagent: When X is chloro, an appropriate reagent is thionyl chloride; when X is bromo, an appropriate reagent is thionyl bromide; when X is iodo, an appropriate reagent is $(C_4H_9)_4NI^{+-}$, on the chloro compound; when X is $O_2SOR$, appropriate reagents are methanesulfonyl chloride, tosyl chloride. Suitable solvents for this reaction step are DMF, $CH_2Cl_2$, pyridine, chloroform and the like; typically the reaction is conducted at from about $-10°$ C. to reflux for from a few minutes to 18 hours. Primal intermediate III is obtained from II (R' is not $NH_2$) by treatment with $PCl_5$ to give the imino chloride which with methanol gives the iminoether, which is hydrolyzed to the free amine, III.

The $\Delta^2$ isomer is obtained from the $\Delta^3$ isomer by treatment with a base such as triethylamine in a solvent such as methylene chloride for from several minutes to several days at a temperature of from 0° C. to reflux.

The present invention embraces all stereoisomers of the compounds prepared by the above process. However, it is well-known in the bicyclic $\beta$-lactam antibiotic art that certain isomers of a given species are more active than their corresponding enantiomorph. This appears to be true for the instant invention; although the extent of this relationship of antibiotic activity to conformation cannot be stated for all species embraced by the present invention. However, by way of illustration, the following relationship has been established for the species 7-(1-hydroxyethyl)-3-(2-aminoethylthio)-cephalosporanic acid (I):

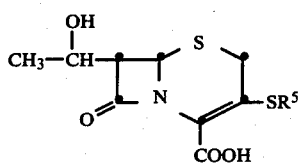

Because of the regio-specific synthesis, detailed-above, there are only 4 stereoisomers of interest:

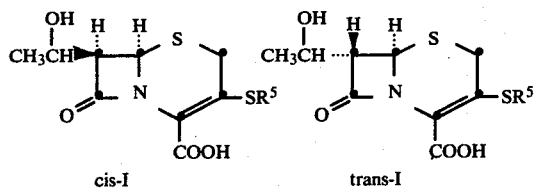

For each configuration, cis or trans, there are two stereoisomers. For example, relative to the cis configuration there are the following diastereomers:

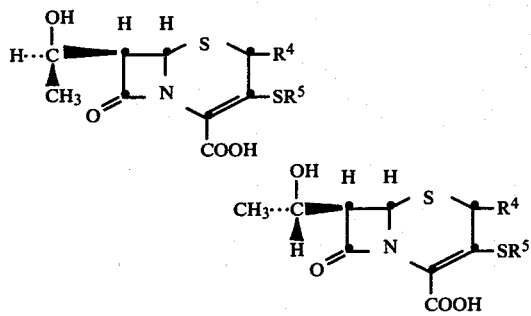

Correspondingly, there are two trans isomers. The absolute configuration of the isomers is not known; however, any given isomer may unambiguously be identified by physical parameters.

Pharmaceutically acceptable salts which may be formed using procedures well known to the art from the compounds of the invention include (a) inorganic base salts such as alkali metal, e.g. sodium and potassium, alkaline earth, e.g. calcium, and organic base salts, e.g. procaine and dibenzylethylene diamine salts and (b) acid addition salts, e.g. with hydrochloric, hydrobromic, sulphuric, nitric, phosphoric, toluene-p-sulphonic and methanesulphonic acids. In addition to salts, the novel compounds of the present invention may be administered in the form of esters, including those discussed above. Examples of esters that might be mentioned are esters of alcohols, phenols, mercaptans, and thiophenols of the general formula —COOR$^8$ wherein R$^8$ represents the radical of an alcohol or a thiol such as methyl, ethyl, tertiary butyl, a substituted alkyl such as phthalimidomethyl, succinimidomethyl, phenacyl, a substituted phenacyl for example p-bromophenacyl, a β-substituted ethyl group such as 2,2,2-trichloroethyl, 2-(pmethylphenyl)-ethyl, 2-(p-methylphenyl)sulfonylethyl, 2-methylaminoethyl, 2-chloro(or bromo-)ethyl, methylthioethyl, benzyl, a substituted benzyl group such as p-nitrobenzyl, p-methoxybenzyl, 3,5-dinitrobenzyl, 2,4,6-trimethylbenzyl, p-t-butylbenzyl, m-phenylbenzyl, p-pivalyloxyphenyl, 3,5-dichloro-4-hydroxy-benzyl, and the like, a benzhydryl or substituted benzhydryl group such as p-methoxybenzhydryl, an acyloxyl alkyl group such as acetoxymethyl, pivaloyloxymethyl, an alkoxy group such as methoxymethyl, or a monocyclic aryl group for example phenyl or substituted phenyl such as p-nitrophenyl or 3,5-dinitrophenyl, or unsaturated alkyl such as 3-methyl-butenyl, methallyl, and 3-butenyl and the like. These esters are readily prepared in accordance with processes well known in this art.

The novel compound are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example against *Staphylococcus aureus* (penicillin resistant), *Escherichia coli, Klebsiella pneumoniae, Salmonella typhosa, Pseudomonas* and *Bacterium proteus*. The compounds of the present invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in water-based paints and in the white water of paper mills to inhibit the growth of harmful bacteria.

The products of this invention may be used alone or in combination as the active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstruction with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose aluminum stearate gel or hydrogenated edible fats, emulsifying agents, for example lecithin, sorbitan monooleate or acacia; non-aqueous vehicles, which may include edible oils, for example, almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being tested and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight. The preferred daily dosage for the compounds of the invention range from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. by weight of active ingredient based upon the total weight of the composition; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution. Typical formulations of specific products are described below.

The following examples representatively illustrate; but do not limit the product, process, compositional or method of treatment aspects of the present invention.

EXAMPLE I

Preparation of 7-[1-hydroxyethyl]cephalosporanic Acid

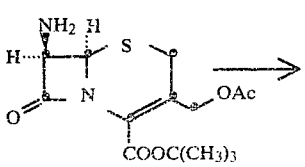

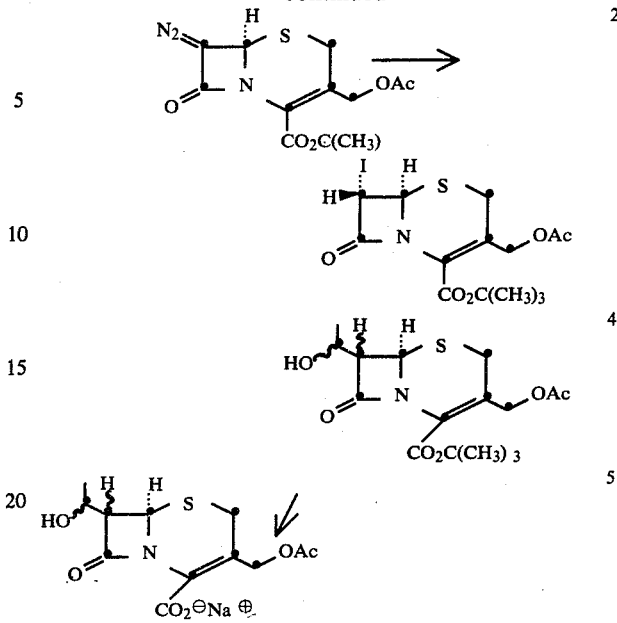

STEP A

Preparation of t-butyl 7-diazocephalosporanate (2)

A mixture of 2.7 g. (8.36 mmoles) of t-butyl 7-aminocephalosporanate (1) prepared according to the literature procedure; [R. J. Stedman, J. Med. Chem., 9, 444 (1966)and 1.15 g. (16.7 mmoles) of sodium nitrite in 120 ml. of methylene chloride and 120 ml. water is cooled to 0° C.–3° C. in an ice/$H_2O$ bath and is treated with 6.24 ml. of 2N sulfuric acid for 50 minutes. The organic phase is separated, dried with anhydrous sodium sulfate, filtered, and concentrated. The concentrate is used immediately for subsequent transformation.

STEP B

Preparation of t-butyl 7-α-iodocephalosporanate (3)

The concentrate of t-butyl 7-diazocephalosporanate (2) obtained from process I is diluted with 180 ml. of acetone, cooled to 0° C.–3° C. in an ice/$H_2O$ bath, and treated with a cold solution of 3.7 ml of 57% hydroiodic acid and 4.76 g. of sodium iodide in 15 ml. of water for 25 minutes. After this time, the mixture is treated with solid sodium bicarbonate, filtered, and evaporated. The residue obtained is partitioned between 150 ml. of ethyl acetate and 125 ml. of 5% aqueous sodium thiosulfate and shaken vigorously. The organic phase is separated, dried with anhydrous magnesium sulfate, and evaporated. Purification by column chromatography on 150 g. of Florosil using benzene-ethyl acetate (10:1) as the eluant gives 1.0 g. (27%) of product 3, which is identified by NMR spectral analysis.

STEP C

Preparation of t-butyl 7-α- & 7-β-[1'-hydroxyethyl]-cephalosporanates (4) as Diastereomeric Mixtures A stirred solution of t-butyl 7-α-iodocephalosporanate (3) 137.5 mg. (0.3 mmoles) in 10 ml. of anhydrous diethyl ether at −70° C. under nitrogen atmosphere is treated with one molar equivalent of a solution of 2.9M methylmagnestumbromide in diethyl ether for 10 minutes. The resulting suspension is then exposed to excess anhydrous acetaldehyde at −70° C. for 15 minutes followed by stirring for an additional 45 minutes. The reaction mixture is quenched at −70° C. with 1.0 ml. of saturated aqueous ammonium chloride and partitioned between diethyl ether and water. The organic phase is separated, dried with anhydrous magnesium sulfate, filtered, and evaporated. Purification of the residue obtained by preparative thin layer chromatography [2 developments benzene-EtOAc (4:1)] gives 19.0 mg. of t-butyl 7-β-[1′-hydroxyethyl]cephalosporanate as a single, crystalline diastereomer; m.p. 154.5° C.-155.5° C. (isopropanol); and 27.5 mg. of t-butyl 7-α-[1′-hydroxyethyl]-cephalosporanate as a mixture of both diastereomers which are separated by high pressure liquid chromatography and characterized by NMR spectroscopy.

EXAMPLE II

Preparation of Sodium 7-β-[1′-hydroxyethyl]cephalosporanate (5)

t-Butyl 7-β-[1′-hydroxyethyl]cephalosporanate (4) 33.0 mg. (0.09 mmoles) is dissolved in 1.0 ml. of cold trifluoroacetic acid and the mixture is stirred at 0° C. for 30 minutes. The trifluoroacetic acid is removed under reduced pressure and the residue obtained is partitioned between chloroform and dilute aqueous sodium bicarbonate. The aqueous phase is separated and acidified to pH 1–2 with 2.5N hydrochloric acid and is extracted with ethyl acetate. The ethyl acetate extract is dried with anhydrous magnesium sulfate, filtered, and evaporated to give 27.0 mg. (97%) of 7-β-[1′-hydroxyethyl]-cephalosporanic acid which is characterized by IR, NMR, and mass spectrum (as disilyl derivative).

The cephalospranic acid is converted to its corresponding sodium salt by treating an aqueous acetone solution of the acid with a solution of one equivalent of sodium bicarbonate in water, removing the acetone under reduced pressure, and lyopholizing the aqueous solution.

In similar fashion each of the other three t-butyl 7-[1-hydroxyethyl]cephalosporanate isomers are converted to the corresponding sodium 7-(1-hydroxyethyl)cephalosporanate.

EXAMPLE 3

Preparation of Benzhydryl 7-methoxy-7-(1-hydroxyethyl)Cephalosporanate

Step A: Preparation of benzhydryl 7,7-dibromocephalosporanate

To a stirred solution of freshly prepared benzhydryl 7-diazocephalosporanate (1.02 g., 2.3 mmoles) in 75 ml. methylene chloride at −70° under nitrogen atmosphere is added dropwise a solution of bromine (368 mg., 2.3 mmole) in 20 ml. methylene chloride during 15 minutes. The mixture is warmed to 0° during 20 mins. and evaporated under reduced pressure. The residue is purified by column chromatography on silica gel to give 280 mg. (21%) benzhydryl 7,7-dibromocephalosporante. Recrystallization from $CH_2Cl_{12}$-$ET_2O$ gives m.p. 127° (dec.).

Analysis Calc. for $C_{23}H_{19}NO_5SBr_2$: Calc.: C, 47.52; H, 3.29; N, 2.41; Br, 27.49. Found: C, 47.62; H, 3.22; N, 2.38; Br, 27.46.

In similar fashion t-butyl-7-diazocephalosporanate is converted to t-butyl 7,7-dibromocephalosporanate.

Step B: Preparation of t-butyl 7-bromo-7-(1-hydroxyethyl)cephalosporanate

By substitution of t-butyl 7,7-dibromocephalosporanate for t-butyl 7-α-iodocephalosporanate in the procedure described in Step C of Example 1 the product obtained is t-butyl 7-bromo-7-(1-hydroxyethyl)cephalosporanate. The benzhydryl ester may be similarly converted.

Step C: Preparation of t-butyl 7-methoxy-7-(1-hydroxyethyl)cephalosporate

To a stirred solution of 1 g. (0.229 mmole) of t-butyl 7-bromo-7-(1-hydroxyethyl)cephalosporanate in 20 ml. of methanol under nitrogen at 22° is added 0.45 g. (0.229 mmole) of silver tetrafluoroborate. Progress of the reaction is followed by thin layer chromatography. When reaction is complete the solution is evaporated under reduced pressure and the residue is purified by column chromatography on silica gel using mixtures of benzene and ethyl acetate.

The benzhydryl ester may be similarly converted.

Step D: Preparation of benzhydryl 7-bromo-7-methoxycephalosporanate

A solution of benzhydryl 7-diazocephalosporanate (0.45 g., 1.0 mmole) in 10 ml. of methanol and 10 ml. methylene chloride containing 0.138 g. (1.0 mmole) of N-bromoacetamide is stirred at 22° until reaction is complete. The solvents are removed under reduced pressure and the residue is chromatographed using ethyl acetate-benzene mixture to afford the desired benzhydryl 7-bromo-7-methoxycephalosporanate.

Step E: Preparation of benzhydryl 7-(1-hydroxyethyl)-7-methoxycephalosporanate

Benzhydryl 7-bromo-7-methoxycephalosporanate is treated with n-butyllithium followed by acetaldehyde according to the procedure of Example 1, Step C to afford the desired benzhydryl 7-(1-hydroxyethyl)-7-methoxycephalosporanate.

EXAMPLE 4

The following chart illustrates the preparation of representative intermediate species of the present invention, which are prepared by analogy to relevant foregoing examples by substitution of reagents, in equivalent amounts, for the reagents of the foregoing example.

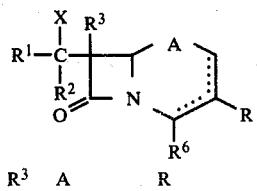

| Compound | $R^1$ | $R^2$ | $R^3$ | A | R | $R^6$ | X |
|---|---|---|---|---|---|---|---|
| 1 | H | $CH_3$ | H | S | $CH_2OAc$ | COOH | OH |
| | | | | | $Ac= \overset{O}{\underset{\|\|}{C}}-CH_3$ | | |
| 2 | H | $C_6H_5-CH_2$ | H | S | $CH_2OAc$ | COOH | OH |
| 3 | H | $CH_3-CH_2$ | H | S | $CH_2OAc$ | $COOCH(C_6H_5)_2$ | OH |
| 4 | H | $CH_3$ | H | O | $CH_2OAc$ | $COOCH(C_6H_5)_2$ | OH |

-continued

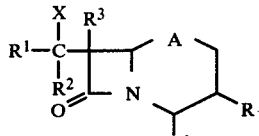

| Compound | R¹ | R² | R³ | A | R | R⁶ | X |
|---|---|---|---|---|---|---|---|
| 5 | H | CH₃ | H | CH₂ | CH₂OAc | COOCH₂—C₆H₄—NO₂ | OH |
| 6 | H | CH₂C₆H₅ | H | CH₂ | CH₂OAc | COOCH(C₆H₅)₂ | OH |
| 7 | H | H | H | CH₂ | CH₂OAc | COOCH(C₆H₅)₂ | OH |
| 8 | H | C₆H₅—CH₂CH₂ | H | CH₂ | CH₂OAc | COOCH(C₆H₅)₂ | OH |
| 9 | H | CH₃ | H | S | CH₂Cl—CH₂OTS | COOH | OH |
| 10 | H | C₆H₅CH₂ | H | S | Ts = Tosyl | COOH | OH |

EXAMPLE 5

Preparation of benzhydryl 7-(1-hydroxyethyl)-3-chloro-3-cephem-4-carboxylate

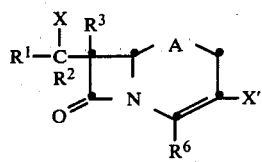

Ia $R^2 = H$
$R^1 = CH_3$
$R^3 = H$
$X = OH$
$A = S$
$X' = Cl$
$R^6 = COOCH(C_6H_5)_2$

Step A

Sodium 7-(1-hydroxyethyl)cephalosporanate (3.5 g.) is dissolved in 100 ml DMSO and added to 4.5 g chromous acetate under N₂. The reaction mixture is stirred overnight at 25° C. The reaction mixture is diluted with water, and extracted with ethyl acetate. The aqueous phase is acidified to pH 2 and extracted with ethylacetate. The ethylacetate extract is dried and evaporated to give 7-(1-hydroxyethyl)-3-methylenecepham-4-carboxylic acid.

Step B 7-(1-Hydroxyethyl)-3-methylenecepham-4-carboxylic acid (3.0 g.) is dissolved in 30 ml. ethylacetate and treated with 2.0 g. of dipenhyldiazomethane. The reaction mixture is allowed to stand overnight at 25° C., and then the solvent is removed under reduced pressure. The residue is chromatogrammed on silica gel to give benzhydryl 7-(1-hydroxyethyl)-3-methyl-enecepham-4-carboxlate.

Step C

Benzhydryl 7-(1-hydroxyethyl)-3-methylene-cepham-4-carboxylate (4.6 g.) is dissolved in 500 ml. of CH₂Cl₂, cooled to −78° and treated with a stream of ozone in oxygen until a blue color persists in the reaction mixture. After 1 minute at −78° the reaction mixture is treated with 5 ml. of dimethyl sulfide and the reaction mixture is allowed to stand at −78° for 20 min. followed by 1 hour at 25° C. The solvent is removed under reduced pressure to give the crude benzhydryl 7-(1-hydroxyethyl)-3-hydroxy-3-cephem-4carboxylate.

Step D

The crude product from the ozonolysis (3.0 g.) is dissolved in 60 ml. DMF cooled to 0° and treated with 15 ml. SOCl₂. The reaction mixture is diluted with ice cold pH 7 buffer and the crude product precipitates out. This is separated from the aqueous phase and taken up in methylene chloride, dried over MgSO₄ and evaporated. The residue is chromatogrammed on silica gel to give benzhydryl 7-(1-hydroxyethyl)-3-chloro-3-cephem-4-carboxylate.

The following table illustrates the preparation of representative intermediate species which are analogous to those prepared in Example 5, Structure 1a.

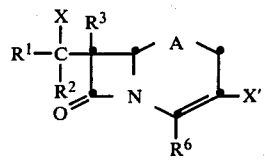

Ia

| COMPOUND | R¹ | R² | R³ | A | X' | R⁶ | X |
|---|---|---|---|---|---|---|---|
| 1 | CH₃ | H | H | CH₂ | Cl | COOH | OH |
| 2 | CH₃ | H | H | S | Cl | COOCH(C₆H₅)₂ | OH |
| 3 | CH₃ | H | H | O | Cl | COOCH₂—C₆H₄—O—NO₂ | OH |
| 4 | CH₃ | H | H | NH | Cl | COOCH(C₆H₅)₂ | OH |
| 5 | H | H | H | CH₂ | Br | COOSi(CH₃)₃ | OH |
| 6 | H | H | H | S | Cl | COOSi(CH₃)₃ | OH |
| 7 | C₆H₅—CH₂ | H | H | S | Cl | COOCH(C₆H₅)₂ | OH |
| 8 | CH₃ | CH₃ | H | S | OMs | COOCH(C₆H₅)₂ | OH |

EXAMPLE 6

Preparation of 3-(2-Aminoethylthio)-7,β-phenylacetamido-3-cephem-4-carboxylic acid $$C_6H_5-CH_2-\overset{O}{\underset{\|}{C}}-NH-\text{[β-lactam]}-SCH_2CH_2NH_2$$
COOH Step A: Trimethylsilyl 3-chloro-7β-phenylacetamido-3-cephem-4-carboxylate 3-Chloro-7,β-phenylacetamido-3-cephem-4-carboxylic acid (0.105 g.) is suspended in 2 ml. dry $CH_2Cl_2$ under nitrogen. Triethylamine (0.042 ml.) (1 eq) is added to make the triethylamine salt and the solution is treated with 0.048 g. (1.5 eq) of trimethylsilyl chloride. The reaction mixture is stirred at 25° C. for 0.5 hour and the solvent and excess reagent are evaporated under reduced pressure to give the trimethylsilyl ester of 3-chloro-7,β-phenylacetamido-3-cephem-4-carboxylic acid.

Step C: Trimethylsilyl 3-(2-aminoethylthio)-7,β-phenyl acetamido-3-cephem-4-carboxylate Trimethylsilyl-3-chloro-7,β-phenylacetamido-3-cephem-4-carboxylate from above is dissolved in 1 ml. anhydrous $CH_2Cl_2$ and 1 ml. anhydrous THF under $N_2$ and the solution is treated with 0.050 g. (1.5 eq) of 2-aminoethanethiol hydrochloride and 0.080 ml. of triethylamine (2.5 eq) is added dropwise over 1 minute. The reaction mixture is stirred at 25° C. under nitrogen for 2 hours to give a solution of trimethylsilyl-3-(2-aminoethylthio)-7,β-phenylacetamido-3-cephem-4-carboxylate. U.v: $\lambda_{max}^{CH2Cl}$ 306 mμ. Evaporation of the solvents under reduced pressure gives a residue which is the above-mentioned ester.

Step D: 3-(2-Aminoethylthio)-7,β-phenylacetamido-3-cephem-4-carboxylic acid

The trimethylsilyl ester from above is treated with 2 ml. of 0.25 molar pH 7 phosphate buffer. A gum is formed which on further stirring gives a solid which is filtered off and washed with water and dried to give 0.046 g. of 3-(2-aminoethylthio)-7,β-phenylacetamido-3-cephem-4-carboxylic acid. U.v. $_{max}^{H2O}$ 282 mμ. E=7100; i.r. (μ); 3.1 (NH), 5.65 (β-lactam), 5.9 (broad, amide and carboxylate), 6.5 (amide II). M.s. (high resolution) M+ 609.1998 (for trisilyl derivative). Calc. for $C_{17}H_{19}N_3O_4S_2$ +3 trimethylsilyl=609.1996.

EXAMPLE 7

3-(2-Aminoethylthio)-7,β-Phenylacetamido-3-Cephem-4-Carboxylic Acid via the corresponding p-Nitrobenzyl-4-carboxylate Step A: p-Nitrobenzyl-3-(2-aminoethylthio)-7,β-phenylacetamido-3-cephem-4-carboxylate p-Nitrobenzyl-3-chloro-7,β-phenylacetamido-3-cephem-4-carboxylate (0.100 g.) is dissolved in 2 ml. anhydrous $CH_2Cl_2$ and 2 ml. anhydrous THF; 0.024 g. of 2-aminoethanethiol hydrochloride, followed by 0.056 ml. of triethylamine are added. The mixture is stirred at 25° C. for 2.5 hours. The reaction mixture is washed once with water, dried and evaporated to give 0.104 g. of crude product which is purified by preparative tlc on silica gel using 25% EtOAc/$C_6H_6$ as eluant. Yield 0.022 g. i.r. (μ): 3.1 (NH), 5.66 (β-lactam), 6.0 (broad, ester and amide), 6.23 (nitro). U.v. $\lambda_{max}^{CH2Cl2}$ 306 mμ (E=11,500). nmr δ: 1.8 E 2.4 ($NO_2-C_6H_4-$); 2.66 ($C_6H_5$); 3.3 d (J=8 cp.s.. N$\underline{H}$—C=O); 4.6 q (J=4.5, J=8, C-7H); 4.75 q, (C$\underline{H}_2$-$C_6H_4NO_2$); 4.93 d (J=4.5, C-6 H); 6.33, s ($C_6H_5C\underline{H}_2$) 6.4-7.3 m (C-2 H and S-C$\underline{H}_2$C$\underline{H}_2$-N$\underline{H}_2$).

Step B: 3-(2-Aminoethylthio)-7,β-Phenylacetamido-3-cephem-4-carboxylic acid p-Nitrobenzyl-3-aminoethylthio-7,β-phenylacetamido-3-cephem-4-carboxylate (0.020 g.) is dissolved in 1 ml. dioxane and 1 ml. $H_2O$; 0.020 g. of 10% Pd/C is added and the mixture hydrogenolyzed at 40 lbs. $H_2$ pressure for 1 hour. The catalyst is filtered off and washed with water. The filtrate and washings are extracted with EtOAc and the aqueous phase is freeze-dried to give the product.

EXAMPLE 8

Preparation of 3-(2-Dimethylaminoethylthio)-7,β-phenylacetamido-3-cephem-4-carboxylic acid Step A: Benzhydryl 3-chloro-7,β-phenylacetamido-3-cephem-4-carboxylate 3-Chloro-7,β-phenylacetamido-3-cephem-4-carboxylic acid (0.352 g) is dissolved in 5 ml. ethyl acetate and treated with 0.200 g. of diphenyldiazo methane and the reaction mixture allowed to stand for 4 hours at 25° C. The solvent is evaporated and the residue is chromatographed on silica gel to give benzhydryl 3-chloro-7,β-phenylacetamido-3-cephem-4-carboxylate.

I.R. μ: 3.02 (NH); 5.60 (β-lactam); 5.78 (ester) 5.91 (amide).

Step B: Benzhydryl-3-(2-dimethylaminoethylthio)-7,β-phenylacetamido-3-cephem-4-carboxylate Benzhydryl-3-chloro-7,β-phenylacetamido-3-cephemcarboxylate (0.050 g.) is dissolved in 1 ml. $CH_2Cl_2$ and 1 ml. THF. Dimethylaminoethanethiol hydrochloride (0.014 g.) is added, followed, followed by 0.013 ml. of triethylamine. The reaction mixture is stirred at 25° C. for 2.5 hours, then diluted with $CH_2Cl_2$ and washed with water. The organic phase is dried and evaporated. The residue on preparative tlc on silica gel gives 0.020 g. of product which is contaminated with its $\Delta^2$ isomer.

I.R. μ: 3.05 (NH); 3.62

$$(N{\overset{CH_3}{\underset{CH_3}{\diagup\!\!\!\diagdown}}});$$

5.6 (β-lactam); 5.71 (ester); 5.95 (amide).

N.M.R. 7.3, s ($C_6H_5$); 6.82 (C$\underline{H}$($C_6H_5)_2$); 4.9–6.0, m (β-lactam protons); 3.6 ($C_6H_5C\underline{H}_2$); 3.46, g (C-2 protons); 2.6, m (S—$CH_2$—$CH_2$—N); 2.13

$$(N{\overset{CH_3}{\underset{CH_3}{\diagup\!\!\!\diagdown}}})$$

M.S. M+587.

Step C: 3-(2-Dimethylaminoethylthio)-7,β-phenylacetamido-3-cephem-4-carboxylic acid Benzhydryl-3-dimethylaminoethylthio-7,β-phenylacetamido-3-cephem-4-carboxylate (0.035 g.) (mixture with $\Delta^2$ isomer) is dissolved in 0.2 ml. anisole, cooled to 0° and treated with 1 ml. TFA at 0°. The mixture is allowed to stand 2 minutes at 0° and then diluted with C$_6$H$_6$ and evaporated. The residue is partitioned between ether and water. The aqueous phase is taken to pH 7 and freeze-dried. The residue is chromatographed by high pressure liquid chromatography, using a Waters' Associate C$_{18}$ Bondapak column and 10% THF in H$_2$O eluant. The product (0.005 g.) is obtained free of the $\Delta^2$ isomer. U.V. $\lambda_{max}^{H2O}$ 2,84, E=6500.

N.M.R. 7.35 (C$_6$H$_5$); 5.56, d, (C-7H); 5.15, d (C-6H); 3.68, s (C$_6$H$_5$CH$_2$); 3.55, g (C-2H); 3.2, m (S-CH$_2$CH$_2$N); 2.85, s (N-CH$_3$) M.S M+493 monosilyl derivative.

EXAMPLE 9

Preparation of 3-(2-Dimethylaminoethylthio)-7,β-(D-mandelylamide)-3-cephem-4-carboxylic acid Step A: 7,β-(D-O-formylmandelylamido)-3-methylenecepham-4-carboxylic acid 7-Amino-3-methylenecepham-4-carboxylic acid (2.14 g.) is dissolved in 20 ml. of H$_2$O and 20 ml. acetone and treated with 1.68 g. of NaHCO$_3$. The reaction mixture is cooled to 0° C. and treated with D-O-formylmandelyl chloride (2.1 g.) in 10 ml. acetone, added dropwise over 15 minutes. The reaction mixture is stirred at 0° for ½ hour and then allowed to warm to 25° C. and stirred for 1 hour. The reaction mixture is diluted with water, adjusted to pH 7 with 5% NaHCO$_3$ and extracted with ethyl acetate. The aqueous phase is taken to pH 2 and extracted with ethyl acetate. The ethyl acetate extract is dried and evaporated to give the product.

Step B: Benzhydryl 7,β-(D-O-formylmandelylamido)-3-methylenecepham-4-carboxylate The crude acid from above is dissolved in 40 ml. ethyl acetate and treated with 2.5 g. of diphenyldiazomethane. The reaction mixture is allowed to stand at 25° C. overnight. The solvent is removed under reduced pressure and the residue is chromatogrammed on silica gel to give 0.53 g. of product.

I.R. μ: 3.05 (NH); 5.62 (β-lactam); 5.75 (ester); 5.9 (amide).

N.M.R.: 8.05 (H—C=O); 7.3, s (C$_6$H$_5$); 6.93, s (C$_6$H$_5$)$_2$C—O);
|
H 6.2 (O—CH—C=O); 5.56, q (c-7 H); 5.3, d (C-6 H); 5.15, d (C=CH$_2$); 3.2 q (C-2 HO).

Step C: Benzhydryl 7,β-(D-O-formylmandelylamido)-3-chlorocephem-4-carboxylate

Benzhydryl 7,β-(D-O-formulmandelylamido)-3-methylenecepham-4-carboxylate (0.842 g) is dissolved in 100 ml. CH$_2$Cl$_2$ cooled to −78° C. and treated with ozone until a blue color persists in the reaction mixture. Dimethylsulfide (1 ml.) is then added and the reaction mixture is maintained at −78° C. for 20 minutes and then 1.5 hours at 25° C. The solvent is removed under reduced pressure to given benzhydryl 7,β-(D-O-formylmandelylamido)-3-oxo-cepham-4-carboxylate, which is dissolved in 20 ml. DMF and cooled to 0° C.

Thionyl chloride (0.4 ml.) is added and the mixture is allowed to stir for 45 minutes at 25° C. Water (ice cold) (40 ml.) and pH 7 buffer (10 ml.) is added and the mixture is stirred vigorously. A solid precipitates out which is filtered off, washed with a little water, taken up in CH$_2$Cl$_2$, dried over MgSO$_4$ and evaporated. The residue is chromatogrammed on silica gel (30 g.) using 15% EtoAc/C$_6$H$_6$ to give 0.230 g of the product.

N.M.R. δ: 8.0, s,

(HC);

7.3, s ($_6$H$_5$); 7.0, s ((C$_6$H$_5$)$_2$CH—); 6.2, s (O—CH—C=O); 5.7, g (C-7 H); 4.8, d (C-6H); 3.37, g (C-2 H).

Step D: Benzhydryl 7,β-(D-Mandelylamido)-3-(2-dimethylaminoethylthio)-3-cephem-4-carboxylate Benzhydryl 7,β-(D-O-formylmandelylamido)-3-chlorocephem-4-carboxylate (0.050 g) is dissolved in 1 ml. CH$_2$Cl$_2$ and 1 ml. THF. 2-Dimethylaminoethanethiol hydrochloride (0.015 g.) is added followed by 0.028 ml. of Et$_3$N. The reaction mixture is stirred at 25° C. for 1.5 hours under N$_2$. The reaction mixture is diluted with CH$_2$Cl$_2$ washed with water, dried and evaporated. The residue is purified by preparative tlc to give the product (0.018 g) as a mixture of $\Delta^2$ and $\Delta^3$ compounds.

I.R. μ: 3.0 (NH); 3.6

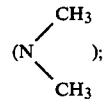

5.6 (β-lactam); 5.69 (ester) 5.9 (amide).

N.M.R.: 7.3, s (C$_6$H$_5$); 6.9, s ((C$_6$H$_5$)$_2$CH—O); 5.0-6.0, m. (β-lactam) and

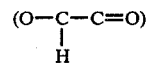

2.8, m (S-CH$_2$—CH$_2$—N); 2.15, s (N-CH$_3$).

Step E: 3-(2-Dimethylaminoethylthio)-7,β-(D-mandelylamido) 3-cephem-4-carboxylate acid Benzhydryl 7,β-(D-mandelylamido)-3-(2-dimethylaminoethylthio)-3-cephem-4-carboxylate (0.025 g.) is dissolved in 0.2 ml. anisole, cooled to 0° C. and treated with 1 ml. of TFA at 0° for 2 minutes. The TFA is removed under reduced pressure, the residue is taken up in 10 ml. C$_6$H$_6$ and evaporated under reduced pressure to give a residue which is taken up in Et$_2$O and H$_2$O. The aqueous phase is separated, washed once with ether and adjusted to pH 7. with a few drops of 5% NaHCO$_3$. The solution is freeze-dried. The residue is purified HPLC using a Waters C-18 Bondpak column and 10% THF/H$_2$O as eluant to give 0.008 g of the $\Delta^3$ product and 0.013 g of the $\Delta^2$ isomer.

N.M.R.: 7.45, s (C$_6$H$_5$); 5.54, d [c-7 HO); 5.24, s (H—C—OH); 5.15, d (C-6H); 3.55] (C-2H); 3.22, m (—S-CH$_2$—CH$_2$N); 2.82, s (N-CH$_3$)

EXAMPLE 10

The following table illustrates the preparation of representative intermediate species of the present invention, by analogy to relevant foregoing examples.

General structure:

$R^1R^2N$ on C with $R^3$, ring A, lactam N, $SR^5$, $R^6$

| Compound | $R^1$ | $R^2$ | $R^3$ | A | $R^5$ | $R^6$ |
|---|---|---|---|---|---|---|
| 1 | 2-thienyl–CH$_2$–C(=O)– | H | –OCH$_3$ | S | –CH$_3$ | CO$_2$Na |
| 2 | C$_6$H$_5$–CH$_2$–C(=O)– | H | –OCH$_3$ | S | –CH$_2$–CH$_2$–NH$_2$ | CO$_2$H |
| 3 | 2-thienyl–CH$_2$–C(=O)– | H | H | O | –CH$_3$ | –CO$_2$Na |
| 4 | 2-thienyl–CH(CO$_2$H)–CO– | H | H | O | S–CH$_2$–CH$_2$N(CH$_3$)$_2$ | CO$_2$Na |
| 5 | 2-thienyl–CH$_2$–C(=O)– | H | H | CH$_2$ | –S–CH$_2$–CH$_2$N(CH$_3$)$_2$ | COOH |
| 6 | C$_6$H$_5$–C(OH)(–)–C(=O)– | H | H | CH$_2$ | –S–CH$_2$–CH$_2$–N(CH$_3$–CH$_3$)$_2$ | COOH |
| 7 | C$_6$H$_5$–CH(NH$_2$)–C(=O)– | H | H | CH$_2$ | –SCH$_3$ | COOH |
| 8 | 2-thienyl–CH$_2$C(=O)– | H | H | O | –S–CH$_2$–CH$_2$–COOH | COONa |

EXAMPLE 11

Following the procedure of Examples 6–9, the 7-(substituted methyl)-3-(substituted thio) species of the present invention are prepared when the indicated substitution of reactants is made:

Reaction scheme: $R^1R^2C(X)$–[ring with $R^3$, A, N, $R^6$, X'] → $R^1R^2C(X)$–[ring with $R^3$, A, N, $R^6$, SR$^5$]

| COMPOUND | $R^1$ | $R^2$ | X | $R^3$ | A | X' | $R^6$ | $R^5$ |
|---|---|---|---|---|---|---|---|---|
| 1 | H | CH$_3$ | OH | H | A | Cl | COOH | CH$_2$–CH$_2$–NH$_2$ |
| 2 | H | C$_6$H$_5$–CH$_2$ | OH | H | S | Cl | COOSi(CH$_3$)$_3$ | CH$_2$–CH$_2$–NH$_2$ |
| 3 | H | CH$_3$CH$_2$ | OH | H | S | Cl | COOCH$_2$–C$_6$H$_4$–NO$_2$ | CH$_2$–CH$_2$–N(CH$_3$)$_2$ |
| 4 | H | CH$_3$ | OH | H | O | Cl | COOH | CH$_2$–CH$_2$–N(CH$_2$CH$_3$)$_2$ |
| 5 | H | CH$_3$ | OH | H | CH$_2$ | Cl | COOH | CH$_2$–CH$_2$–NH$_2$ |
| 6 | H | H | OH | H | CH$_2$ | Cl | COOH | CH$_2$–CH$_2$–N(CH$_3$)$_2$ |
| 7 | H | C$_6$H$_5$–CH$_2$ | OH | H | O | Cl | COOH | CH$_2$–CH$_2$–N(CH$_2$CH$_3$)$_2$ |
| 8 | H | CH$_3$ | OH | H | S | Cl | COOH | CH$_3$ |

EXAMPLE 12

Preparation of Pharmaceutical Compositions

One such unit dosage form consists in mixing 120 mg. of 7-α-[1'-hydroxyethyl]-1-carba-1-dethia-3-[2'-aminoethyl]-ceph-3-ene-4-carboxylic acid with 20 mg. of lactose and 5 mg. of magnesium stearate and placing the 145 mg. mixture into a No. 3 gelatin capsule. Similarly, by employing more of the active in-gredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| 7-α-[1'-hydroxyethyl]-1-carba-1-dethia-3-[2'-aminoethylthio]-ceph-3-ene-4-carboxylic acid | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with a 15% cornstarch paste (6 mg.) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
|---|---|
| Ampoule: | |
| 7-α-[1'-hydroxyethyl]-1-carba-1-dethia-3-[2'-aminoethylthio]-ceph-3-ene-4-carboxylic acid | 500 mg. |
| Diluent: Sterile Water for Injection | 2 ml. |

| OPTHALMIC SOLUTION | |
|---|---|
| 7-α-[1'-hydroxyethyl]-1-carba-1-dethia-3-[2'-aminoethylthio]-ceph-3-ene-4-carboxylic acid | 100 mg. |
| Hydroxypropylmethyl Cellulose | 5 mg. |
| Sterile Water | to 1 ml. |

| OTIC SOLUTION | |
|---|---|
| 7-α-[1'-hydroxyethyl]-1-carba-1-dethia-3-[2'-aminoethylthio]-ceph-3-ene-4-carboxylic acid | 100 mg. |
| Benzalkonium Chloride | 0.1 mg. |
| Sterile Water | to 1 ml. |

| TOPICAL OINTMENT | |
|---|---|
| 7-α-[1'-hydroxyethyl]-1-carba-1-dethia-3-[2'-aminoethylthio]-ceph-3-ene-4-carboxylic acid | 100 mg. |
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients as, for example, with other antibacterical agents such as lincomycin, a penicillin, streptomycin, novobiocin, gentamicin, neomycin, colistin and danamycin, or with other therapeutic agents such as probenecid.

What is claimed is:

1. A compound having the structural formula:

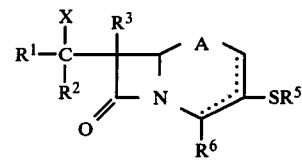

and the non-toxic, pharmaceutically acceptable salt derivatives thereof; wherein the dotted line indicates provision for both $\Delta^2$ and $\Delta^3$ embodiments; $R^1$ and $R^2$ are independently selected from the group consisting of hydrogen, substituted and unsubstituted: lower alkyl having 1-6 carbon atoms, phenyl, benzyl, phenethyl, and thienylmethyl wherein the ring and chain substituents on $R^1$ and $R^2$ are selected from the group consisting of hydroxyl, amino, and carboxyl;

X is OH, SH, $NH_2$, O and =NH;

$R^3$ is hydrogen, methoxy and lower alkylthio;

$R^5$ is selected from the group consisting of: hydrogen; formyl; —$(CH_2)_nY$ wherein n is an integer from 1 to 6 and Y is selected from the group consisting of: hydrogen, hydroxyl, halogen, mercapto, carboxyl, azido, amino, N-loweralkyl amino, N,N-diloweralkylamino, acyloxy and acylthio wherein said acyl is a loweralkanoyl having from 2 to 6 carbon atoms: substituted and unsubstituted; phenyl and 1H-tetrazol-5-yl wherein the substituent is amino, carboxyl, hydroxyl or lower alkyl having 1 to 6 carbon atoms;

$R^6$ is COOH; and

A is S, or SO.

2. A compound having the structural formula:

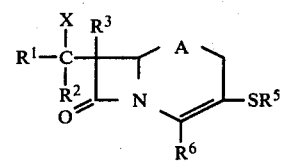

and the pharmaceutically acceptable salt derivatives thereof wherein:

$R^5$ is —$CH_3$, phenyl,

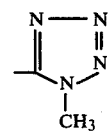

—$CH_2CH_2COOH$, —$CH_2CH_2NH_2$, or —$CH_2CH_2N(CH_3)_2$;

A is S, or SO;

X is OH, SH, or $NH_2$; and $R_3$ is hydrogen, or methoxy.

3. A compound having the following structural formula:

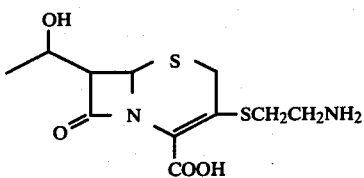

and the pharmaceutically acceptable salt derivatives thereof.

4. A compound according to claim 2 wherein A is S.

5. A compound according to claim 4 wherein $R^1$ is hydrogen; X is hydroxyl.

6. An antibacterial pharmaceutical composition comprising a therapeutically effective amount, in unitary dosage form, of a compound according to claim 1 and a pharmaceutical carrier therefor.

* * * * *